US012354275B2

(12) United States Patent
Liang et al.

(10) Patent No.: US 12,354,275 B2
(45) Date of Patent: Jul. 8, 2025

(54) SYSTEM AND METHOD FOR REGION BOUNDARY GUIDANCE OVERLAY FOR ORGAN

(71) Applicant: EDDA TECHNOLOGY, INC., Princeton, NJ (US)

(72) Inventors: Cheng-Chung Liang, West Windsor, NJ (US); Guo-Qing Wei, Plainsboro, NJ (US); Li Fan, Belle Mead, NJ (US); Xiaolan Zeng, Princeton, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 214 days.

(21) Appl. No.: 18/158,360

(22) Filed: Jan. 23, 2023

(65) Prior Publication Data

US 2024/0249417 A1     Jul. 25, 2024

(51) Int. Cl.
| | |
|---|---|
| *G06T 7/12* | (2017.01) |
| *A61B 34/10* | (2016.01) |
| *G06T 17/20* | (2006.01) |
| *G06T 19/00* | (2011.01) |

(52) U.S. Cl.
CPC ............... *G06T 7/12* (2017.01); *A61B 34/10* (2016.02); *G06T 17/20* (2013.01); *G06T 19/00* (2013.01); *A61B 2034/105* (2016.02); *A61B 2034/107* (2016.02); *G06T 2207/20021* (2013.01); *G06T 2207/30056* (2013.01); *G06T 2210/41* (2013.01); *G06T 2219/004* (2013.01)

(58) Field of Classification Search
CPC .......... G06T 7/12; G06T 17/20; G06T 19/00; G06T 2207/20021; G06T 2207/30056; G06T 2210/41; G06T 2219/004; A61B 34/10; A61B 2034/105; A61B 2034/107
See application file for complete search history.

(56) References Cited

U.S. PATENT DOCUMENTS

| | | | | |
|---|---|---|---|---|
| 5,889,524 | A * | 3/1999 | Sheehan | G06T 17/20 345/419 |
| 6,301,496 | B1 * | 10/2001 | Reisfeld | A61B 5/287 600/407 |
| 11,416,069 | B2 * | 8/2022 | Luo | G06T 15/08 |
| 2003/0048936 | A1 * | 3/2003 | Fan | G06T 7/11 382/131 |
| 2003/0099390 | A1 * | 5/2003 | Zeng | G06T 7/0012 382/173 |

(Continued)

OTHER PUBLICATIONS

International Search Report and Written Opinion mailed Apr. 30, 2024 in International Patent Application No. PCT/US2024/012362.

*Primary Examiner* — Motilewa Good-Johnson
(74) *Attorney, Agent, or Firm* — Venable LLP

(57) ABSTRACT

The present teaching relates to method, system, medium, and implementations for region boundary identification and overlay display. An input associated with a 3D object is received. A 3D volumetric model is obtained for the 3D object with multiple regions, each of which includes multiple labeled voxels. A mesh representation is generated for the surface of the 3D object. Region boundaries on surface of the 3D object are identified based on the 3D volumetric model and the mesh representation. The 3D object is rendered, and the region boundaries are overlaid on the rendered 3D object.

15 Claims, 14 Drawing Sheets

(56) References Cited

U.S. PATENT DOCUMENTS

| | | | |
|---|---|---|---|
| 2005/0219245 A1* | 10/2005 | Tao | G06T 17/20 |
| | | | 345/424 |
| 2008/0123927 A1* | 5/2008 | Miga | A61B 90/36 |
| | | | 382/131 |
| 2012/0209106 A1 | 8/2012 | Liang et al. | |
| 2013/0129170 A1* | 5/2013 | Zheng | G06T 7/149 |
| | | | 382/131 |
| 2014/0073907 A1 | 3/2014 | Kumar et al. | |
| 2016/0058521 A1* | 3/2016 | Liang | G06T 19/00 |
| | | | 703/11 |
| 2020/0380675 A1 | 12/2020 | Golden et al. | |
| 2021/0264623 A1* | 8/2021 | Tandon | A61B 5/4806 |
| 2021/0346091 A1 | 11/2021 | Haslam et al. | |
| 2023/0054394 A1* | 2/2023 | Luo | A61B 90/50 |
| 2023/0225800 A1* | 7/2023 | Grund | A61B 5/366 |
| | | | 600/523 |

* cited by examiner

SYSTEM AND METHOD FOR REGION BOUNDARY GUIDANCE OVERLAY FOR ORGAN

BACKGROUND

1. Technical Field

The present teaching generally relates to computers. More specifically, the present teaching relates to signal processing.

2. Technical Background

With the advancement of computer related technologies, more and more types of information are now analyzed using computers to identify and visualize relevant features to enhance a user's understanding of important aspects of the information and to facilitate the user to accordingly make appropriate decisions. Different industries have benefited from such technological advancement, including the medical industry, where large volume of image data, capturing anatomical information of a patient, may be processed to identify regions of interest (e.g., organs, bones, blood vessels, or abnormal nodule), obtain measurements for each region of interest (e.g., dimension of a nodule growing in an organ), and visualize relevant features (e.g., three-dimensional (3D) visualization of an abnormal nodule). Such techniques have enabled healthcare workers (e.g., doctors) to use high-tech means to assist them in treating patients in a more effective manner.

In recent years, techniques have been developed to assist medical workers to obtain presurgical plans prior to a surgery based on analytics derived from images or provide on-the-fly visualization of anatomical structures inside a patient's body in order to guide surgeons during medical procedures. For example, partial hepatectomy is a surgery to remove part of the liver of a patient to cut off, e.g., a cancer growing in the liver. For this type of procedure, presurgical planning may be performed to identify a region in a liver that needs to be resected. Such a pre-planned resection region may be identified in an offline process and may be marked as such so that it may be used during the procedure as a reference for the surgeon to carry out the operation.

Although existing 3D visualization tools may be used to visualize anatomical structures, such general tools do not provide functionalities tailored to certain medical procedures that require information be presented in certain ways in order to provide useful guidance. Partial hepatectomy procedure is one of such procedures. For example, to remove a cancer in the liver, it will be helpful for a surgeon to see, on-the-fly, where is the intended resection locations on the real time display of what the sensor sees inside the patient's body. Lacking such tools, a surgeon has to rely on general knowledge about the liver anatomy as well as memory to mentally map the pre-planned resection boundaries to the actual liver, not only making it more difficult but also often resulting in inconsistent surgical performance.

Thus, there is a need for a solution that addresses the challenges discussed above.

SUMMARY

The teachings disclosed herein relate to methods, systems, and programming for information management. More particularly, the present teaching relates to methods, systems, and programming related to hash table and storage management using the same.

In one example, a method, implemented on a machine having at least one processor, storage, and a communication platform capable of connecting to a network for region boundary identification and overlay display. An input associated with a 3D object is received. A 3D volumetric model is obtained for the 3D object with multiple regions, each of which includes multiple labeled voxels. A mesh representation is generated for the surface of the 3D object. Region boundaries on surface of the 3D object are identified based on the 3D volumetric model and the mesh representation. The 3D object is rendered, and the region boundaries are overlaid on the rendered 3D object.

In a different example, a system is disclosed for region boundary identification and overlay display. The system includes a 3D region volume modeling unit, a mesh-based region boundary determiner, and a region boundary overlay display unit. The 3D region volume modeling unit is configured for receiving an input associated with a three-dimensional (3D) object with multiple regions therein and obtaining a 3D volumetric model characterizing the 3D object, wherein the 3D object includes multiple regions, each of which occupies a plurality of voxels in the 3D volumetric model, and voxels of each of the multiple regions have the same label. The mesh-based region boundary determiner is configured for generating a 3D surface mesh representation characterizing the surface of the 3D object, wherein the 3D surface mesh representation comprises a plurality of connected geometric units and identifying region boundaries on the surface of the 3D object based on the 3D surface mesh representation and the 3D volumetric model. The region boundary overlay display unit is configured for rendering the 3D object on a two-dimensional (2D) display device and overlaying the region boundaries of the 3D object on the rendered 3D object.

Other concepts relate to software for implementing the present teaching. A software product, in accordance with this concept, includes at least one machine-readable non-transitory medium and information carried by the medium. The information carried by the medium may be executable program code data, parameters in association with the executable program code, and/or information related to a user, a request, content, or other additional information.

Another example is a machine-readable, non-transitory and tangible medium having information recorded thereon for region boundary identification and overlay display. The information, when read by the machine, causes the machine to perform the following steps. An input associated with a 3D object is received. A 3D volumetric model is obtained for the 3D object with multiple regions, each of which includes multiple labeled voxels. A mesh representation is generated for the surface of the 3D object. Region boundaries on surface of the 3D object are identified based on the 3D volumetric model and the mesh representation. The 3D object is rendered, and the region boundaries are overlaid on the rendered 3D object.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
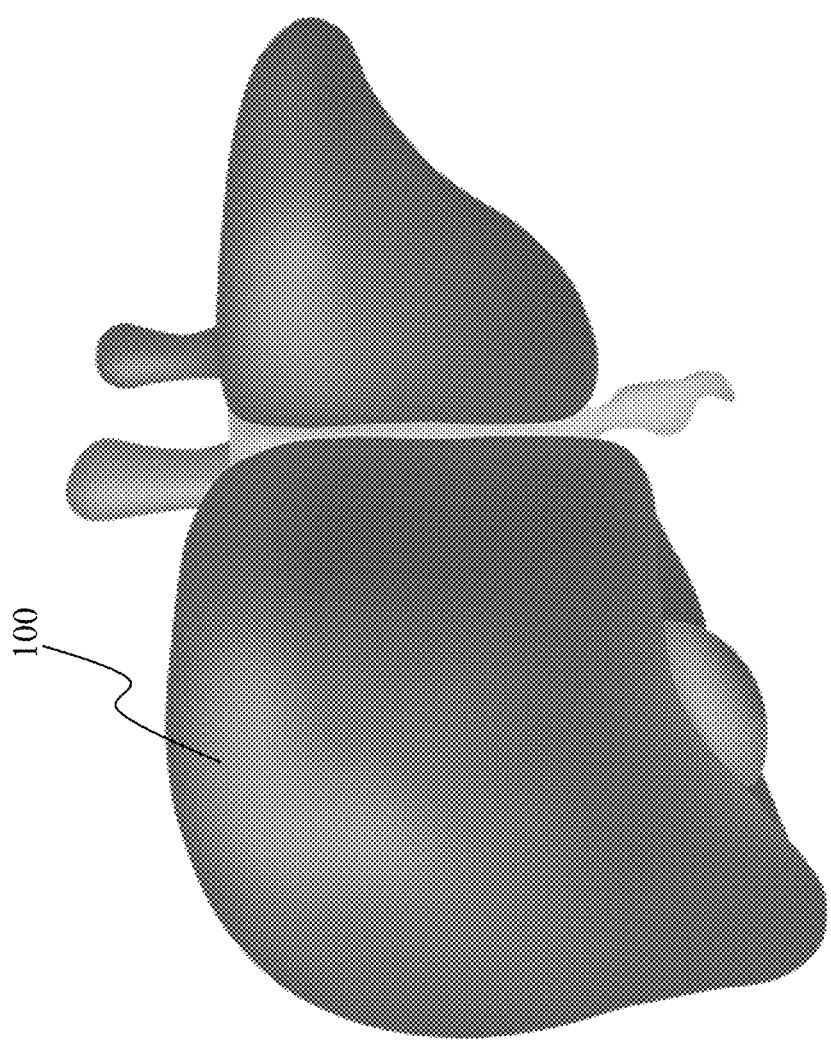
FIG. 1A shows a human liver.

In the following detailed description, numerous specific details are set forth by way of examples in order to facilitate a thorough understanding of the relevant teachings. However, it should be apparent to those skilled in the art that the present teachings may be practiced without such details. In other instances, well known methods, procedures, components, and/or system have been described at a relatively high-level, without detail, in order to avoid unnecessarily obscuring aspects of the present teachings.

The present teaching discloses exemplary methods, systems, and implementations for identifying regional boundaries on the surface of an 3D object where the regional boundaries segregate different structural regions inside the 3D object. Such an 3D object may correspond to an organ such as a liver. The identified regional boundaries of the 3D object may be visualized by superimposing on a rendering of the 3D object. In some embodiments, the regional boundaries may be overlaid on a 3D rendering of the 3D object. In some embodiments, the regional boundaries may be projected onto 2D images of the object.

The regional boundaries may be visualized with respect to a particular perspective, which may be determined in accordance with the perspective used to render the 3D object. In some embodiments, when the 3D object is visualized as 2D images, the perspective may be determined based on the perspective of a camera used to capture the 2D images. When the 3D object is rendered in 3D, the perspective used to visualize the regional boundaries may be determined based on pose parameters used in visualize the 3D object.

In some applications of the present teaching, the 3D object may correspond to a human organ such as a liver. Regions in such an object may correspond to liver lobes. Regional boundaries in this case delineate delineating adjacent lobes of the liver. In applying the present teaching to partial hepatectomy procedure, a part of a liver to be removed corresponds to a resection region and regional boundaries of a resection region represent the boundaries between lobes to be removed. During a partial hepatectomy procedure, region boundaries of a resection region may be identified and visualized by overlaying such boundaries onto a rendering of the resection region. This may be done in real time in a continuous manner so that it effectively provides a visualization that helps a user to always see the location of the part of the liver that is intended to be removed.

The present teaching utilizes different representations of a 3D object to determine locations of boundaries that separate different regions of the 3D object. The present teaching may also be applied to a particular region of a 3D object such as a resection region to determine locations of region boundaries that separate different regions of the given particular region of the 3D object. In some embodiments, the 3D object (or 3D region) may first be modeled using a volumetric representation, which characterizes the 3D object/region in terms of a 3D space the object occupies, represented using, e.g., a plurality of volumetric units such as voxels in the 3D space. A 3D object/region may include subparts, e.g., a liver has multiple lobes, and each of the subparts may also be represented by some volumetric units included in the volumetric representation. That is, a sub-group of volumetric units of the volumetric representation representing a subpart of the 3D object. Each subpart may be labeled differently so that volumetric units belonging to different subparts have different labels. For example, each of liver lobe may be given a different label.

A 3D object may also be characterized in terms of its surface, which may be modeled by, e.g., a mesh representation. In some embodiment, such a mesh representation may include a plurality of surface units, each of which may model a corresponding patch of the object surface, where each patch may have a corresponding sub-surface, which may be approximated as a plane and represented by, e.g., a triangle, a square, or a rectangle. Each of such planar sub-surface, when modeled by a geometric construct (triangle, square, or a rectangle) may include multiple vertices. For instance, a sub-surface (or a patch) may approximately be represented using a 2D triangle with three vertices or a rectangle with four vertices.

Regional boundaries may be identified on the surface of an object. This may be particularly useful in medical field. For example, an organ may include different anatomical parts (e.g., a liver has different lobes) but such anatomical parts may not be visually obvious from the surface of the organ. The present teaching discloses solutions to identify regional boundaries on the surface of an object which separate adjacent sub-regions of the 3D object. In some embodiments, such regional boundaries may be identified by assigning labels to vertices of geometric units in a mesh representation based on regional labels assigned to different 3D regions that interface with the vertices. If a geometric unit such as a triangle has its vertices assigned with different labels, it means that the triangle is on a regional boundary because it interfaces with more than one sub-region of the 3D object. All such geometric units identified this way form regional boundaries. Details of the present teaching is discussed below with reference to different figures. Although the disclosure below uses a liver as an example of a 3D object to illustrate relevant concepts, it is merely for illustration purpose instead of limitation. The present teaching and related concepts may be used for other types of objects.

Figure 1B:
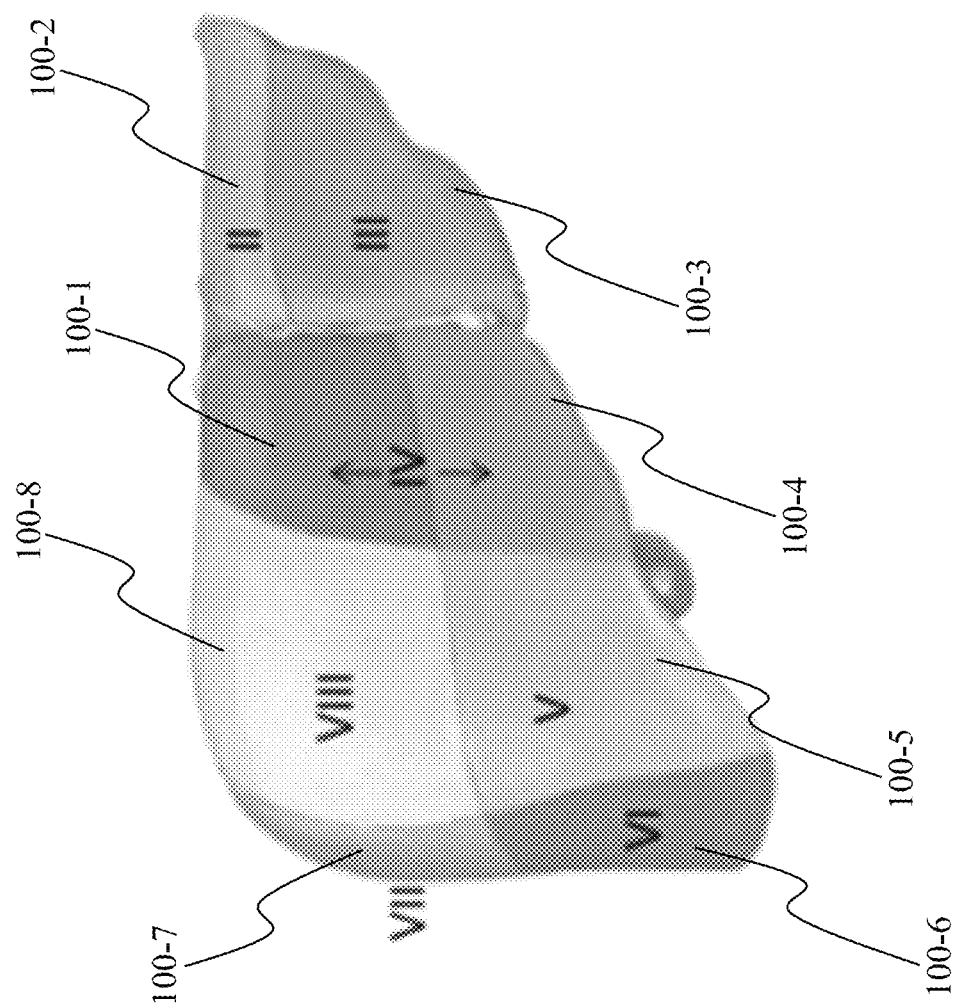
FIG. 1B shows that a human liver with different lobes.
Figure 1D:
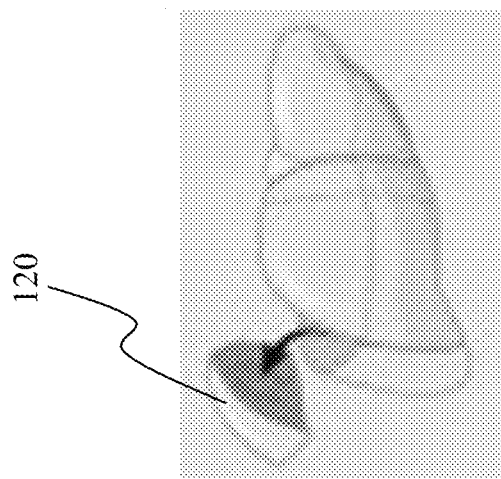
FIG. 1D illustrates resection of a portion of a liver that has a malignant growth therein.
Figure 1C:
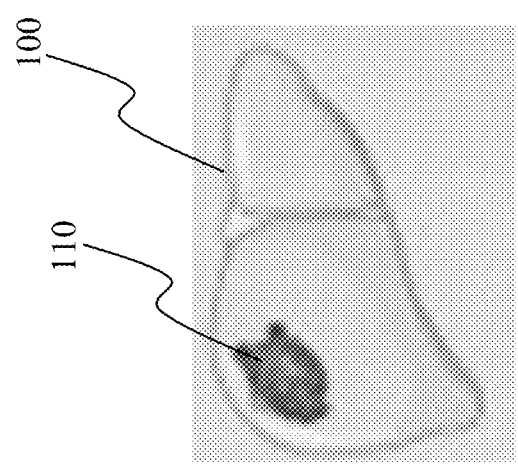
FIG. 1C shows an example organ with a malignant growth therein.

FIG. 1A illustrates a human liver 100 which typically has multiple lobes. As shown in FIG. 1B, a liver includes two main lobes, one on each side. Each main lobe includes 8 lobes, i.e., 100-1, 100-2, ..., 100-7, and 100-8. In general, each lobe may be defined as regions that have relatively independent blood supply network. In some situations, a person may have a growth inside his/her liver, as shown in FIG. 1C, where a growth 110 is present in liver 100. Such a growth may need to be removed when, e.g., it is malignant. Depending on the spread of the growth, certain region(s) of the liver may have to be cut out. For example, if a cancerous growth has been spread to two adjacent lobes, a hepatectomy surgical procedure may be performed to cut out these two lobes. This is called resection and FIG. 1D visually illustrates the concept, where the region 120 resected is the diseased area which may include multiple lobes.

Figure 1F:
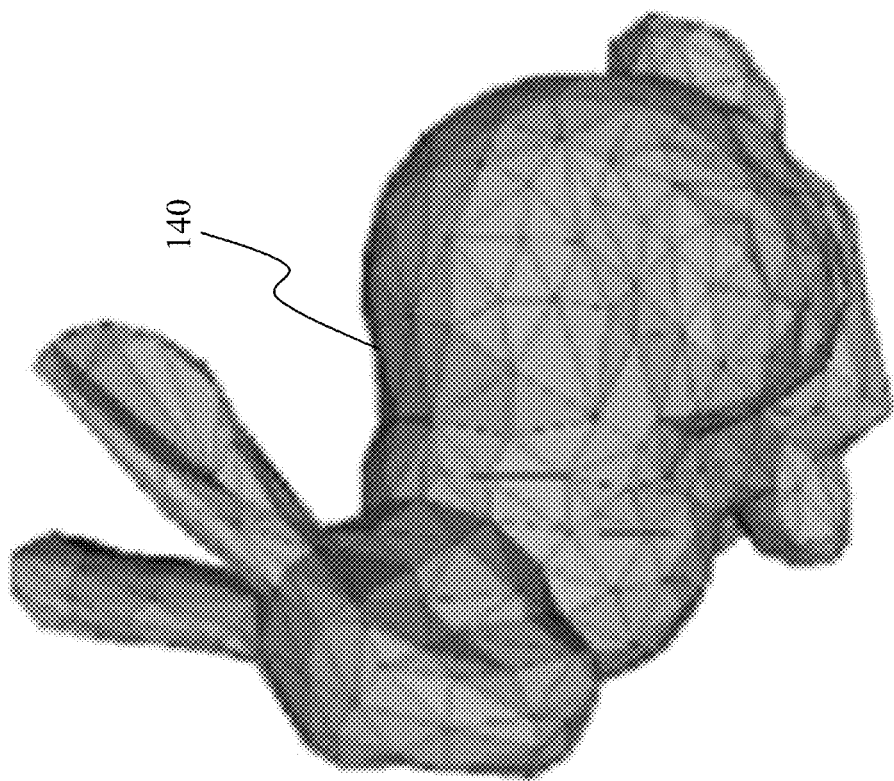
FIG. 1F shows a mesh representation of an object.
Figure 1E:
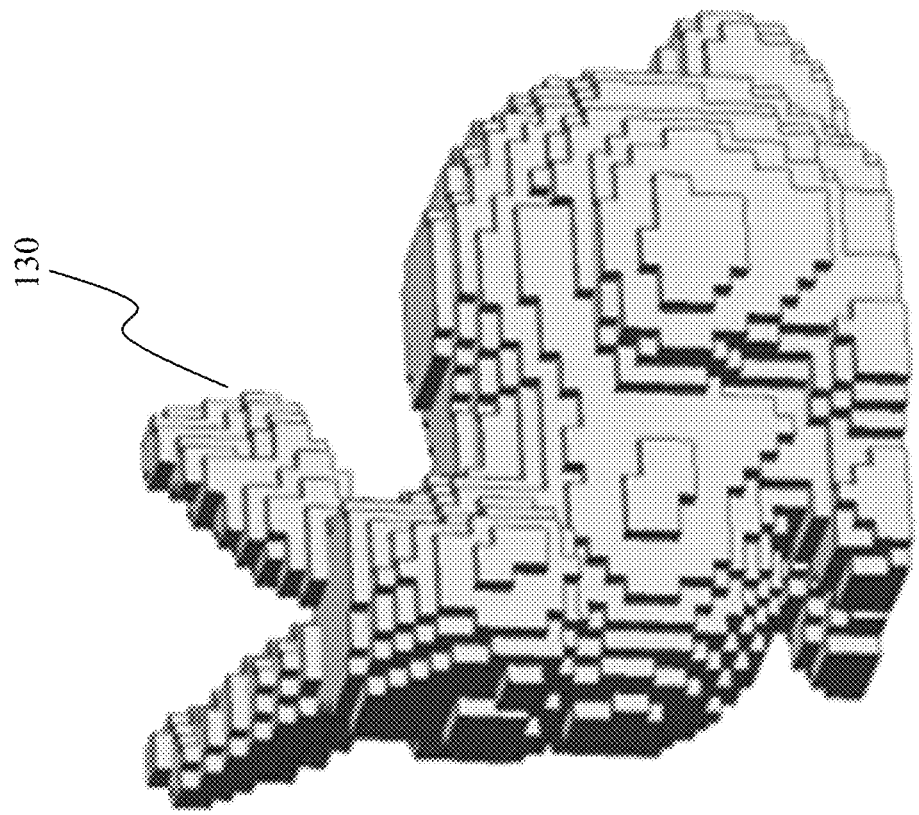
FIG. 1E shows a volumetric representation of an object.

As discussed herein, the present teaching utilizes different representations of an object to identify regional boundaries that separate adjacent regions of the 3D object. The different representations include, e.g., a volumetric representation of the 3D object and a mesh representation of the surface of the 3D object. As discussed herein, the representations may also be obtained for a particular region of the 3D object, e.g., for a resection region of a liver. FIG. 1E shows an exemplary volumetric representation 130 of a 3D object, that includes multiple volume units, each of which represents a unit region occupied by the object. FIG. 1F shows an exemplary mesh representation 140 modeling the surface of the 3D object. The mesh representation 140 may include a plurality of 2D connected geometric units, each of which has a shape and is used to approximate a patch on the surface of the object. In this example, each patch on the surface of the object is modeled using a triangle (a geometric unit) with three vertices. As can be seen herein, the volumetric representation models a 3D object as a solid, while the mesh representation models the same 3D object based on its 3D surface.

Figure 1G:
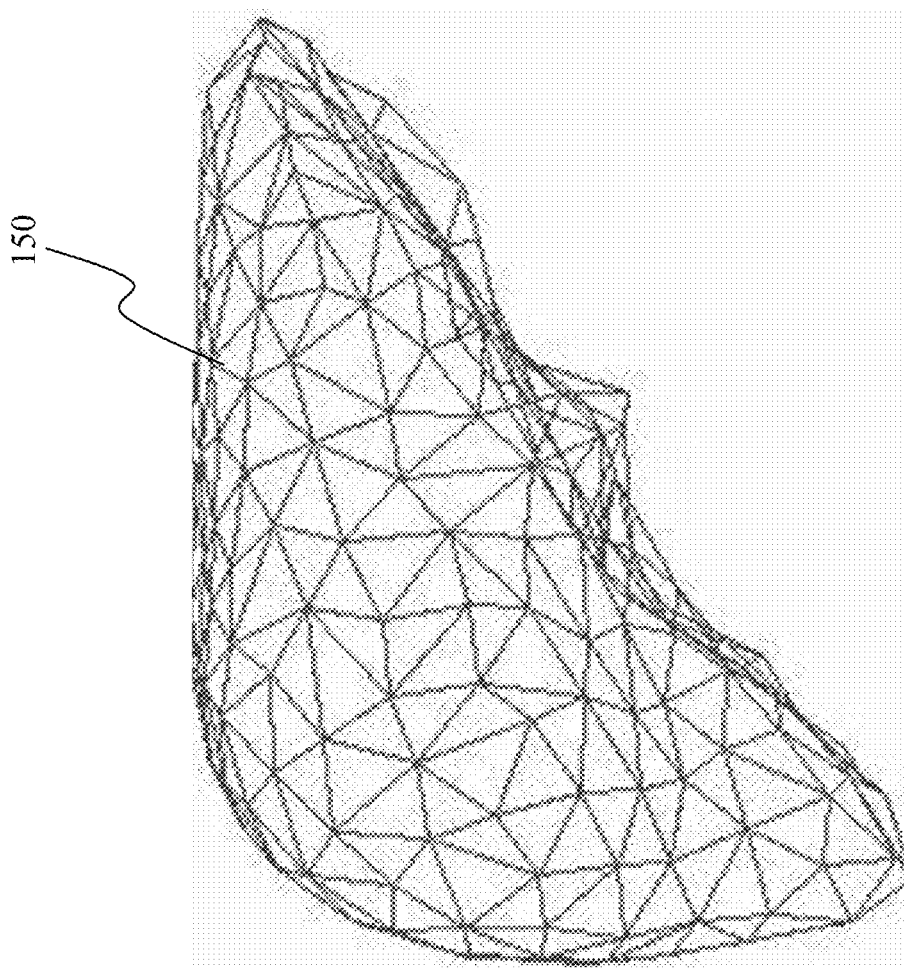
FIG. 1G shows a mesh representation of a human liver.

Using the example of a human liver, both volumetric and mesh representations for a liver may be derived. In some embodiments, its volumetric 3D representation may be obtained via 3D modeling based on, e.g., image data. Lobes of a liver may be identified via segmentation based on, e.g., blood vessels networks. Each segmented 3D lobe is formed by a plurality of voxels which may be identified via labeling. Voxels of adjacent lobes may be assigned distinct labels, as shown in FIG. 1B. Segmentation of a 3D object including a liver and/or volumetric representation of a 3D object (or a portion thereof) may be obtained using any appropriate existing technologies or any techniques developed in the future. The mesh representation for a liver or a portion thereof may also be derived by performing segmentation of the object by analyzing image data to identify the surface of the liver. In some embodiments, the surface of a liver may also be derived based on the volumetric model of the liver. An example mesh representation 150 for a liver is shown in FIG. 1G, where the mesh representation is constructed using triangles to model different patches on the liver surface.

As discussed herein, 3D volumetric model and surface mesh representation may also be used to represent a portion of a 3D object. For example, a resection region of a liver may be characterized based on 3D volumetric model and the surface of the resection region may also be characterized using the mesh representation (for the surface of the liver instead of the interior of the liver due to resection). As such, the approach for identifying regional boundaries on the surface of a liver may also be applied to detect the regional boundaries on the surface of a portion (resection region) of the liver. In a partial hepatectomy procedure, a resection region may be identified, either automatically or manually by a surgeon through interactions with a system facilitating identification of the lobes to be removed. In this case, the resection region may also include multiple lobes and regional boundaries may need to be identified from the surface of the resection region.

Figure 2A:
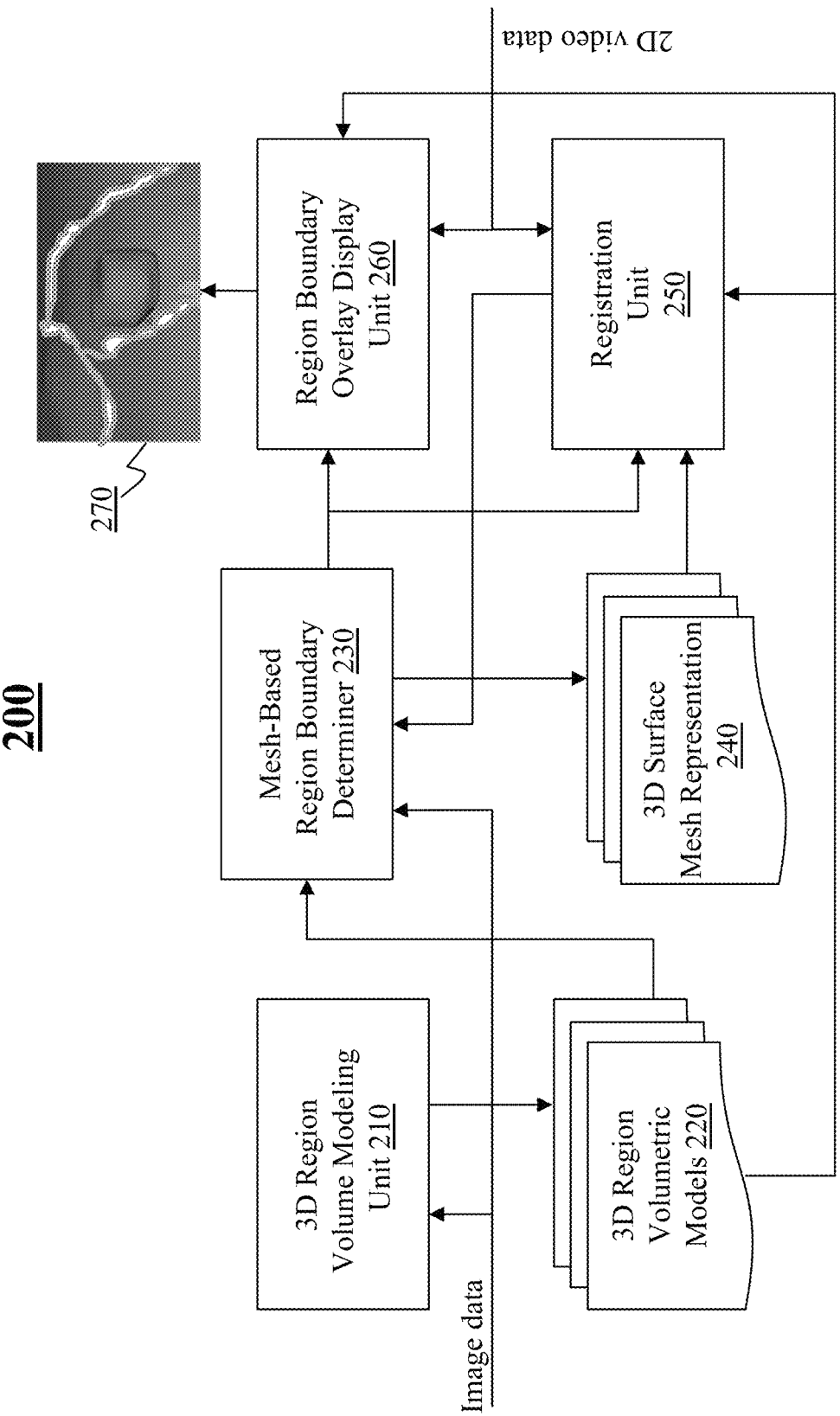
FIG. 2A depicts an exemplary high-level system diagram for a framework for identifying and rendering the boundary of a resection region of an organ, in accordance with an embodiment of the present teaching.

FIG. 2A depicts an exemplary high-level system diagram for a framework 200 for identifying and displaying regional/resection boundaries of an object, in accordance with an embodiment of the present teaching. In this illustrated embodiment, the framework 200 comprises a 3D region volume modeling unit 210, a mesh-based region boundary determiner 230, a registration unit 250, and a region boundary overlay display unit 260. The framework 200 identifies region boundaries on surface of a specified 3D region (either the entire liver or a portion thereof) and overlays the identified region boundaries on a 2D display so that the boundaries of the liver on the surface are visualized to facilitate a user to perform an operation.

The input to the framework 200 may be a 3D model for a liver or for a resection portion of the liver with different lobes labeled. Based on the input, the framework 200 identifies 3D region/resection boundaries on the surface of the liver and then projects the 3D region/resection boundaries on the liver displayed on a 2D display as an overlay. The visualized liver on the 2D display may correspond to a 3D model rendered in a 2D space from a certain perspective or 2D liver images acquired by a laparoscopic camera in order to monitor the location of a medical instrument inserted into the body of a patient as well as the anatomical structure in front of the instrument. The identified region/resection boundaries may be superimposed or overlaid on the displayed liver at corresponding locations determined based on a known perspective and registration. The appropriately visualized resection boundary overlay enables a user (e.g., a surgeon) to see resection boundaries projected on the liver images to facilitate the user to handle the surgical tool in a way to remove the intended part of the liver by following the resection boundaries.

The 3D region volume modeling unit 210 is provided for obtaining 3D volumetric models 220 for the 3D region (either a liver or a resection region). In some embodiments, the 3D region to be modeled may include segmented liver lobes. In some embodiments, 3D region volumetric models 220 may be generated based on image data provided as input by segmenting the liver from images and then further segmenting different lobes based on, e.g., distribution of blood vessel networks recognized from the images. In this case, different lobes so recognized may then be marked using different labels. Such derived 3D region volumetric models 220 are then saved.

The mesh-based region boundary determiner 230 is provided for identify region boundaries. To do so, the mesh-based region boundary determiner 230 generates a 3D mesh representation 240 to model the surface of the liver. As discussed herein, the mesh representation 240 includes a plurality of surface patches, each of which may be approximately represented by a 2D geometric unit with a certain shape. For instance, a triangle may be used to serve as a 2D geometric unit to model each surface patch. In this case, each triangle includes three vertices, and the surface of the liver may be represented by a mesh with connected triangles. Each vertex in the mesh representation interfaces with a voxel in the 3D region volumetric model 220 for the liver. As each voxel in the 3D region volumetric model 220 has a label indicative of the lobe it belongs to, each vertex in the mesh representation may be labeled as well using the label of the voxel that it interfaces with. All vertices in the mesh representation 240 may be assigned labels accordingly. To identify region boundaries, triangles whose vertices have different labels is part of a region boundary of two adjacent lobes.

Figure 3:
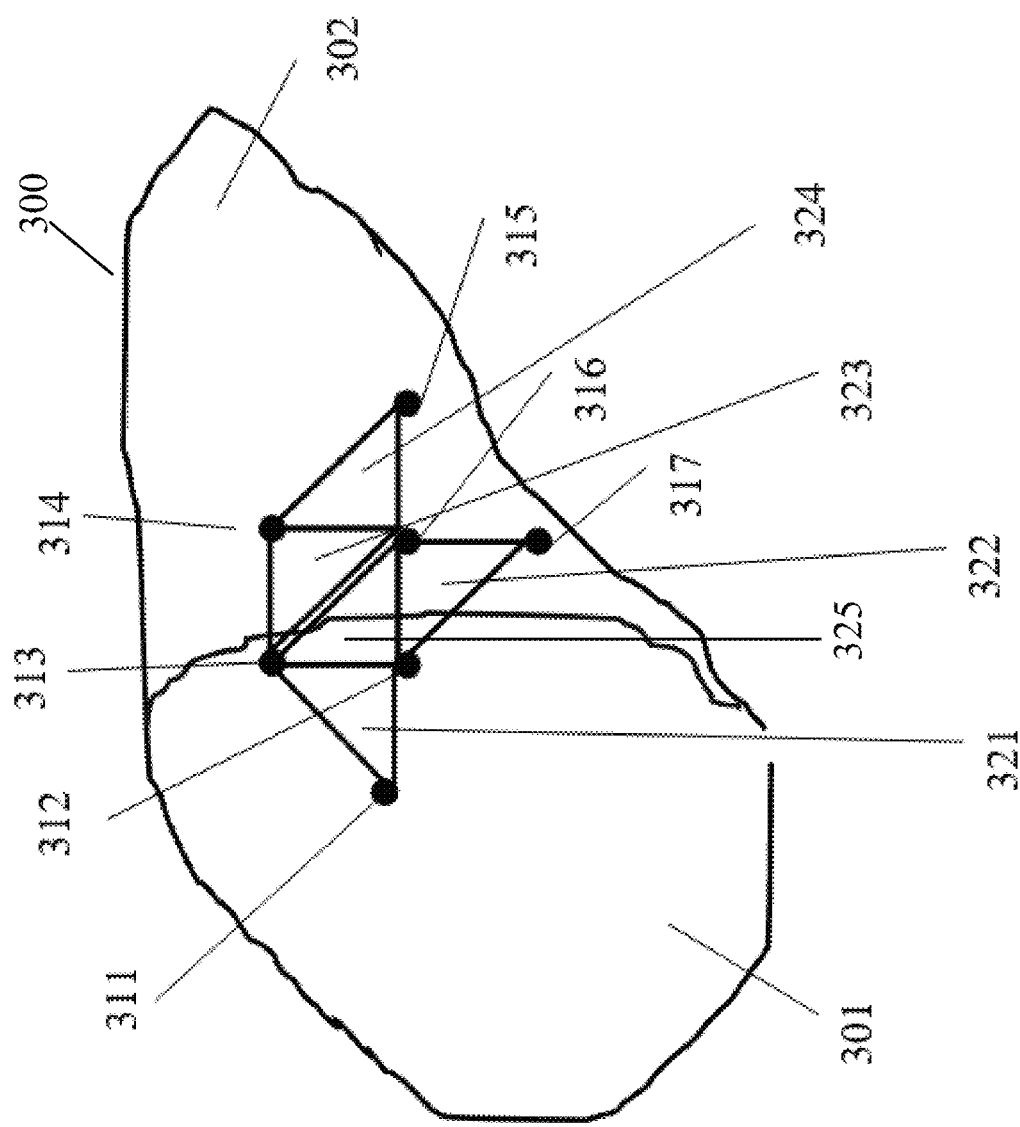
FIG. 3 illustrates the concept of utilizing geometric units forming a surface mesh representation of an organ to identify region boundaries on the surface of the organ, in accordance with an embodiment of the present teaching.

This is illustrated in FIG. 3, where an object 300 (e.g., a liver) has exemplary two regions 301 and 302, each is labeled using a different label. A mesh-based representation may be obtained for the object in accordance with the present teaching with connected triangles, e.g., triangles 321, 322, 323, 324, and 325, that are near a boundary dividing adjacent regions 301 and 302. Each of the triangles has three vertices and neighboring triangles share some of the vertices. For example, triangle 321 has vertices 311, 312, and 313 and vertices 312 and 313 are also vertices of triangle 325. According to the present teaching, as each vertex interfaces with a voxel in a volumetric model for object 300, the label used to label a vertex is determined based on the label of the voxel that the vertex is interfacing. For instance, vertex 312 of triangle 325 interfaces with a voxel in region 301 so that the label for any voxel in region 301 is used to label vertex 312. Similarly, vertex 313 of triangle 325 has the same label as that of vertex 312 because vertex 313 also interfaces with a voxel in region 301. However, as vertex 316 of triangle 325 interfaces with a voxel in region 302, vertex 316 is labeled using the label of its interfacing voxel from region 302. That is, vertex 316 has a different label than that of vertices 312 and 313. So, the three vertices of triangle 325 have different labels. Thus, triangle 325 is recognized as being on a region boundary, dividing adjacent regions 301 and 302. For the same reason, as vertices of both triangles 322 and 323 have different labels, they are also on a region boundary dividing region 301 and region 302, as shown in FIG. 3.

The triangles so identified form region boundaries. The region boundary overlay display unit 260 is provided to overlay the region boundaries over the liver rendered on a 2D display. In some embodiments, the triangles in the region boundaries are superimposed on registered corresponding locations of the rendered liver on the 2D display. An example of such display is shown in 270. As discussed herein, in some embodiments, the liver rendered on the 2D display may correspond to 2D video images acquired by, e.g., a laparoscopic camera during a partial hepatectomy procedure. In this case, the region boundaries represented by a plurality of triangles may be registered, by the registration unit 250, with the corresponding locations on the 2D video images. In some embodiments, the liver may be visualized by rendering its 3D model on the 2D display device. In this case, the region boundaries are overlaid over the rendered 3D liver. In some embodiments, the 3D model of the liver may be rendered on the 2D display device to register with real-time 2D video images acquired in real-time so that the rendered liver has the same perspective as that of the camera that captures the 2D video images. In this case, the region boundaries may then be registered with the rendered 3D liver so that triangles on the boundaries can be superimposed on registered corresponding locations.

Figure 2B:
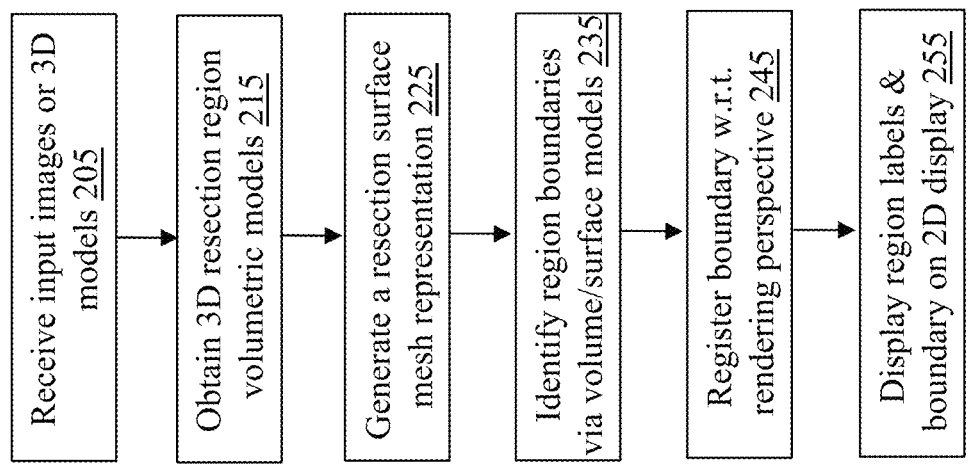
FIG. 2B is a flowchart of an exemplary process for a framework for identifying and rendering the boundary of a resection of an organ, in accordance with an embodiment of the present teaching.

FIG. 2B is a flowchart of an exemplary process of framework 200 for identifying and rendering region boundaries of an object (liver or resection region), in accordance with an embodiment of the present teaching. Input is first received at 205. In some embodiments, input may correspond to a 3D model of the object having segmented regions with labels. In some embodiments, the input may correspond to image data, from which the object and regions included therein may be recognized and labeled. Based on the input, the 3D region volume modeling unit 210 may obtain, at 215, 3D region volumetric models 220. As discussed herein, the 3D region volumetric models 220 represent the object in terms of 3D space it occupies, represented by a plurality of voxels in the 3D space. Voxels in different segmented regions (e.g., lobes) are assigned using different labels. The mesh-based region boundary determiner 230 may generate, at 225, a 3D surface mesh representation 240 to represent the surface of the object. The surface mesh representation 240 may be derived based on either image data inputted, a 3D model of the object, or the generated 3D region volumetric models 220. As discussed herein, the mesh-based representation may be constructed to include a plurality of connected geometric units such as triangles.

Based on the 3D region volumetric models 220 and the mesh-based surface representation 240, the mesh-based region boundary determiner 230 identifies, at 235, region boundaries based on triangles in the mesh-based surface representation 240 that have vertices with different labels. To display the identified resection boundaries on a 2D display, the registration unit 250, performs needed registration, at 245, and the region boundary overlay display unit 260 displays, at 255, the registered regions boundaries onto the 2D display device with, e.g., different regions (lobes) being marked with different labels.

Figure 4A:
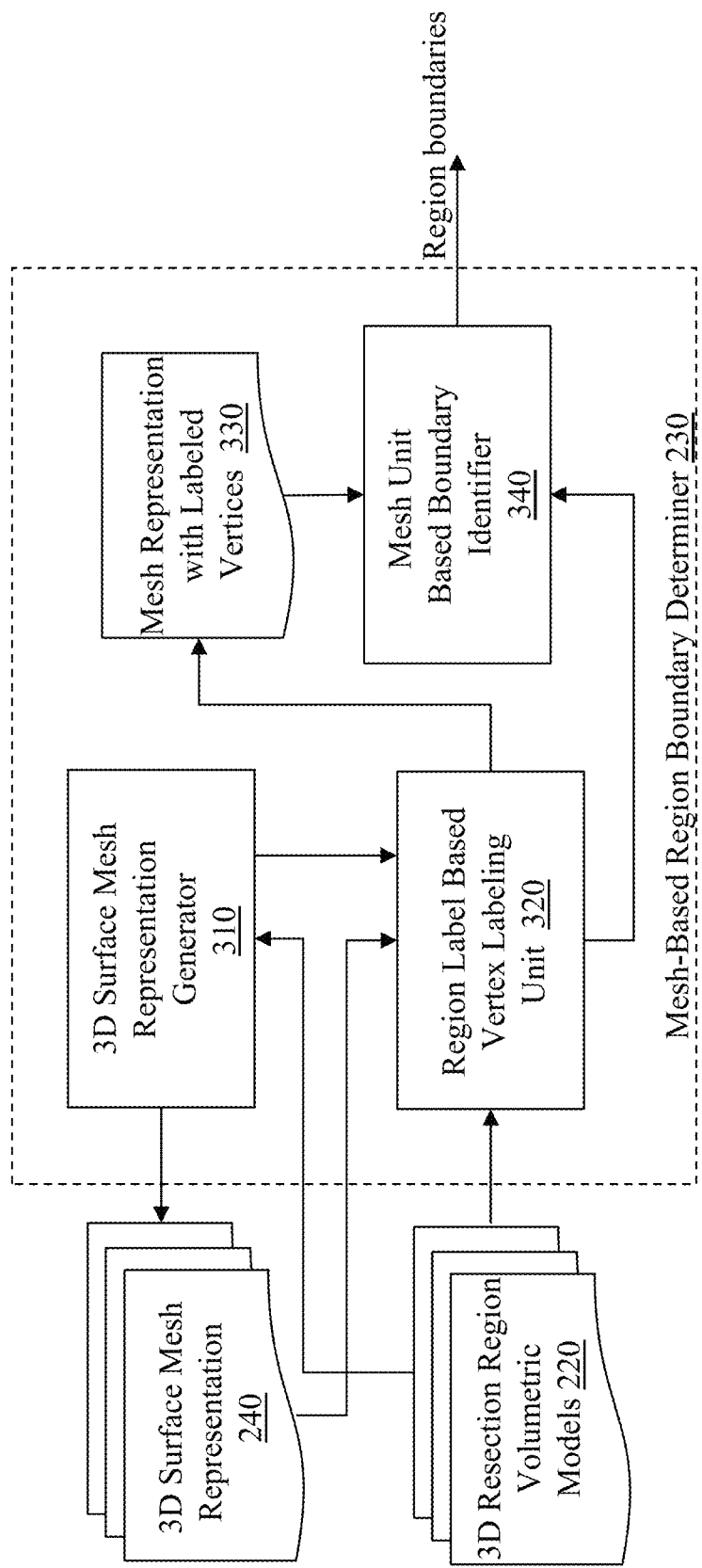
FIG. 4A depicts an exemplary high-level system diagram of a mesh-based region boundary determiner, in accordance with an embodiment of the present teaching.

FIG. 4A depicts an exemplary high-level system diagram of the mesh-based region boundary determiner 230, in accordance with an embodiment of the present teaching. As discussed herein, the mesh-based region boundary determiner 230 identifies boundaries between adjacent regions of an object. In this illustrated embodiment, the mesh-based region boundary determiner 230 comprises a 3D surface mesh representation generator 310, a region label based vertex labeling unit 320, and a mesh unit based boundary identifier 340.

Figure 4B:
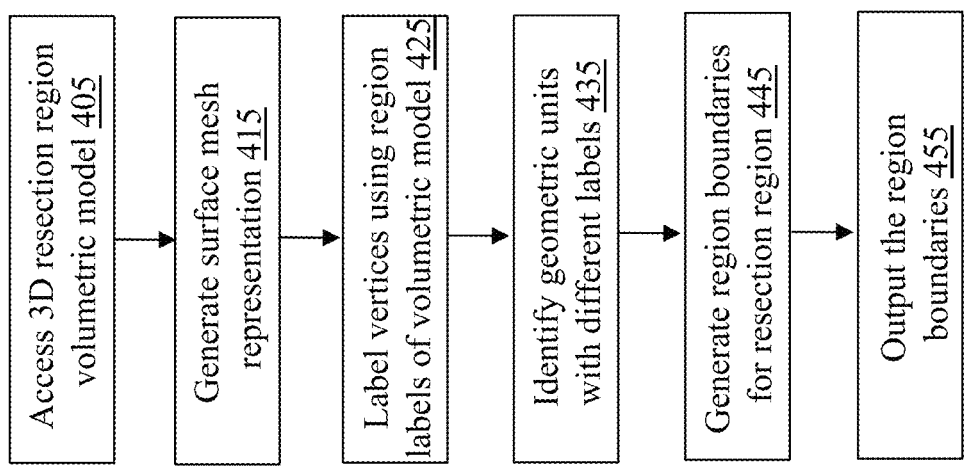
FIG. 4B is a flowchart of an exemplary process of a mesh-based region boundary determiner, in accordance with an embodiment of the present teaching.

FIG. 4B is a flowchart of an exemplary process of the mesh-based region boundary determiner 230, in accordance with an embodiment of the present teaching. In operation, the 3D surface mesh representation generator 310 receives, at 405, input to be used for generating a mesh representation modeling the surface of the 3D object. Upon receiving the input, the mesh representation is generated at 415. In some embodiments, the 3D surface mesh representation 240 may be obtained based on a 3D model of the object. In some embodiments, the 3D resection region volumetric models 220 may also be used for obtaining the 3D surface mesh representation.

As discussed herein, the 3D surface mesh representation 240 may be constructed to include a plurality of mesh units, each of which may correspond to a geometric shape such as a triangle or a rectangle with multiple vertices. The region label based vertex labeling unit 320 is invoked to label, at 425, each of the vertices in the 3D surface mesh representation. Specifically, for each of the vertices, a label assigned to an interfacing voxel in the 3D region volumetric models 220 is used to label the vertex. Once all vertices are labeled, the mesh unit based boundary identifier 340 operates to identify, at 435, mesh units (or triangles in this example) that have different labels on their vertices. Such identified mesh units are then categorized, at 445, as the region boundaries. The mesh unit based boundary identifier 340 then outputs, at 455, such identified region boundaries.

Figure 5:
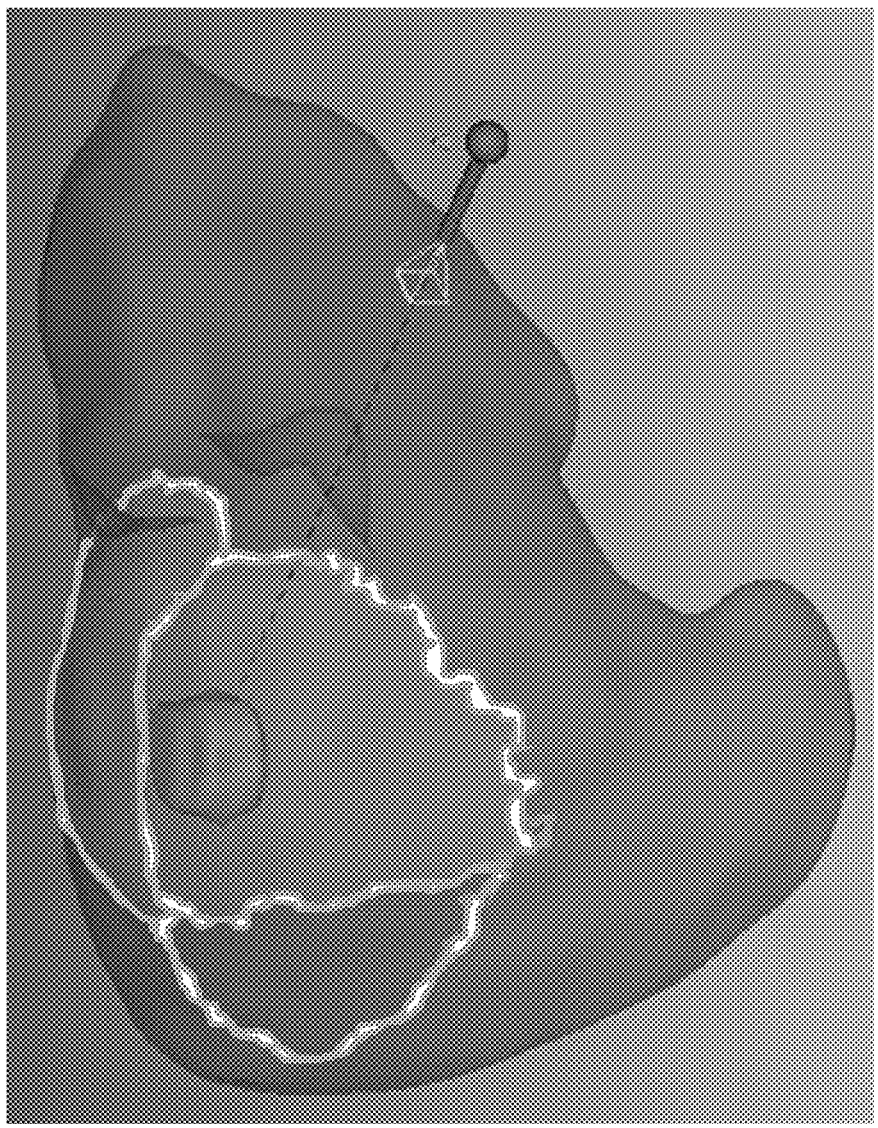
FIG. 5 shows a two-dimensional (2D) display with a rendered organ having different anatomical regions and overlay region boundaries identified in accordance with an embodiment of the present teaching.
Figure 6:
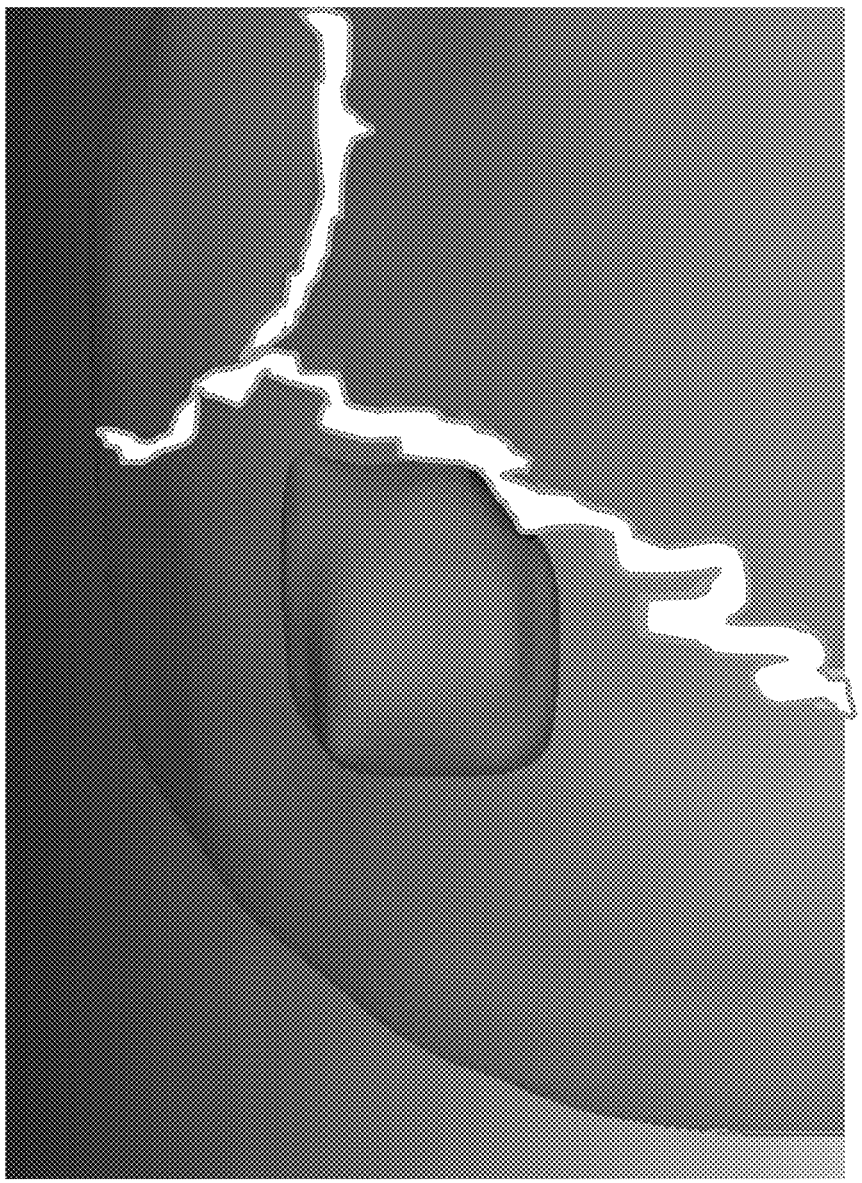
FIG. 6 shows a close-up view of rendered overlay region boundaries around a malignant growth in an organ, in accordance with an embodiment of the present teaching.

FIG. 5 shows a visualization of a 3D liver with an abnormal growth with overlay resection region boundaries, in accordance with an embodiment of the present teaching. In this example, the resection region includes multiple lobes around the abnormal growth and the region boundaries for such lobes that are identified according to the present teaching are visualized. This visualization provides focused view of the resection boundaries to a user without diverting attention to regions that are not part of the resection. In some embodiments, region boundaries for other regions not affected by the procedure may also be visualized. When all region boundaries are visualized, appropriate visualization markings may be applied to highlight the resection area and the relevant region boundaries. In some embodiments, any part of the resection area may be enlarged to show more details. This may further assist a user to have a close-up view of the details of an important area. FIG. 6 illustrates a close-up view of a specific part of the resection region near the abnormal growth.

Figure 7:
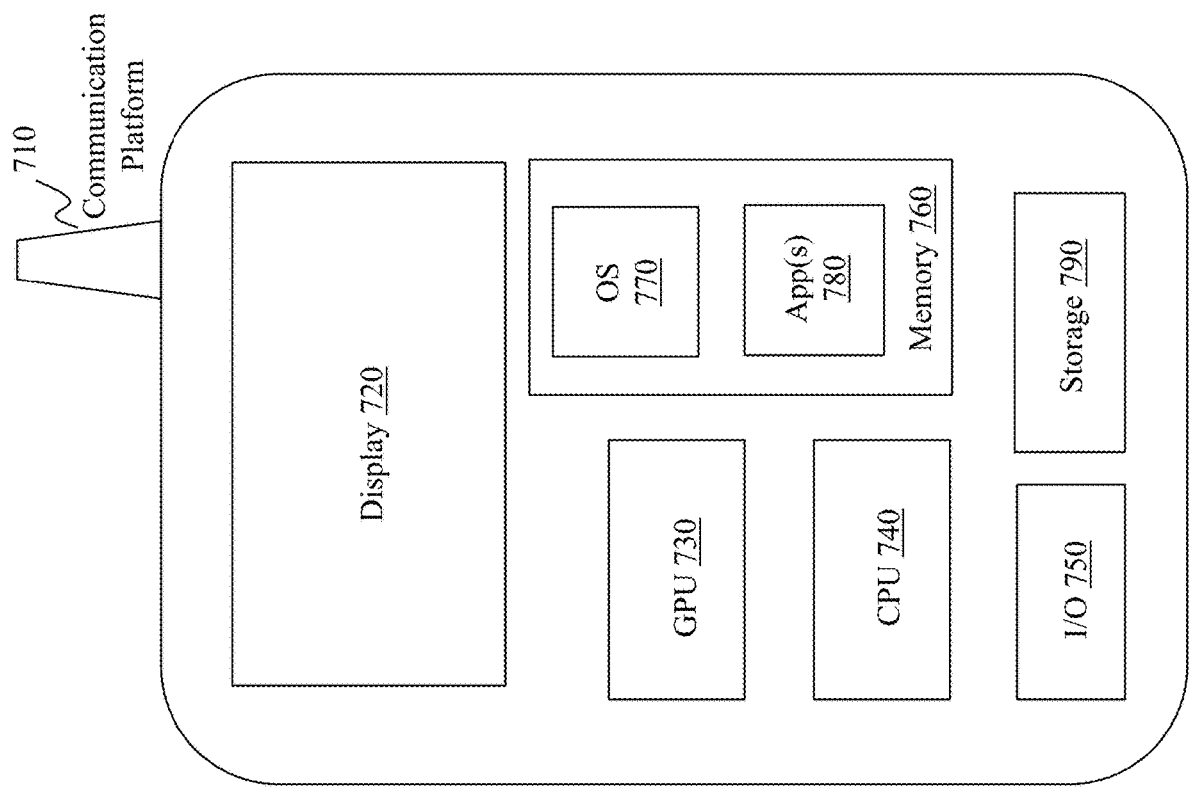
FIG. 7 is an illustrative diagram of an exemplary mobile device architecture that may be used to realize a specialized system implementing the present teaching in accordance with various embodiments.

FIG. 7 is an illustrative diagram of an exemplary mobile device architecture that may be used to realize a specialized system implementing the present teaching in accordance with various embodiments. In this example, the user device on which the present teaching may be implemented corresponds to a mobile device 700, including, but not limited to, a smart phone, a tablet, a music player, a handled gaming console, a global positioning system (GPS) receiver, and a wearable computing device, or in any other form factor. Mobile device 700 may include one or more central processing units ("CPUs") 740, one or more graphic processing units ("GPUs") 730, a display 720, a memory 760, a communication platform 710, such as a wireless communication module, storage 790, and one or more input/output (I/O) devices 750. Any other suitable component, including but not limited to a system bus or a controller (not shown), may also be included in the mobile device 700. As shown in FIG. 7, a mobile operating system 770 (e.g., iOS, Android, Windows Phone, etc.), and one or more applications 780 may be loaded into memory 760 from storage 790 in order to be executed by the CPU 740. The applications 780 may include a user interface or any other suitable mobile apps for information analytics and management according to the present teaching on, at least partially, the mobile device 700. User interactions, if any, may be achieved via the I/O devices 750 and provided to the various components connected via network(s).

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar with to adapt those technologies to appropriate settings as described herein. A computer with user interface elements may be used to implement a personal computer (PC) or other type of workstation or terminal device, although a computer may also act as a server if appropriately programmed. It is believed that those skilled in the art are familiar with the structure, programming, and general operation of such computer equipment and as a result the drawings should be self-explanatory.

Figure 8:
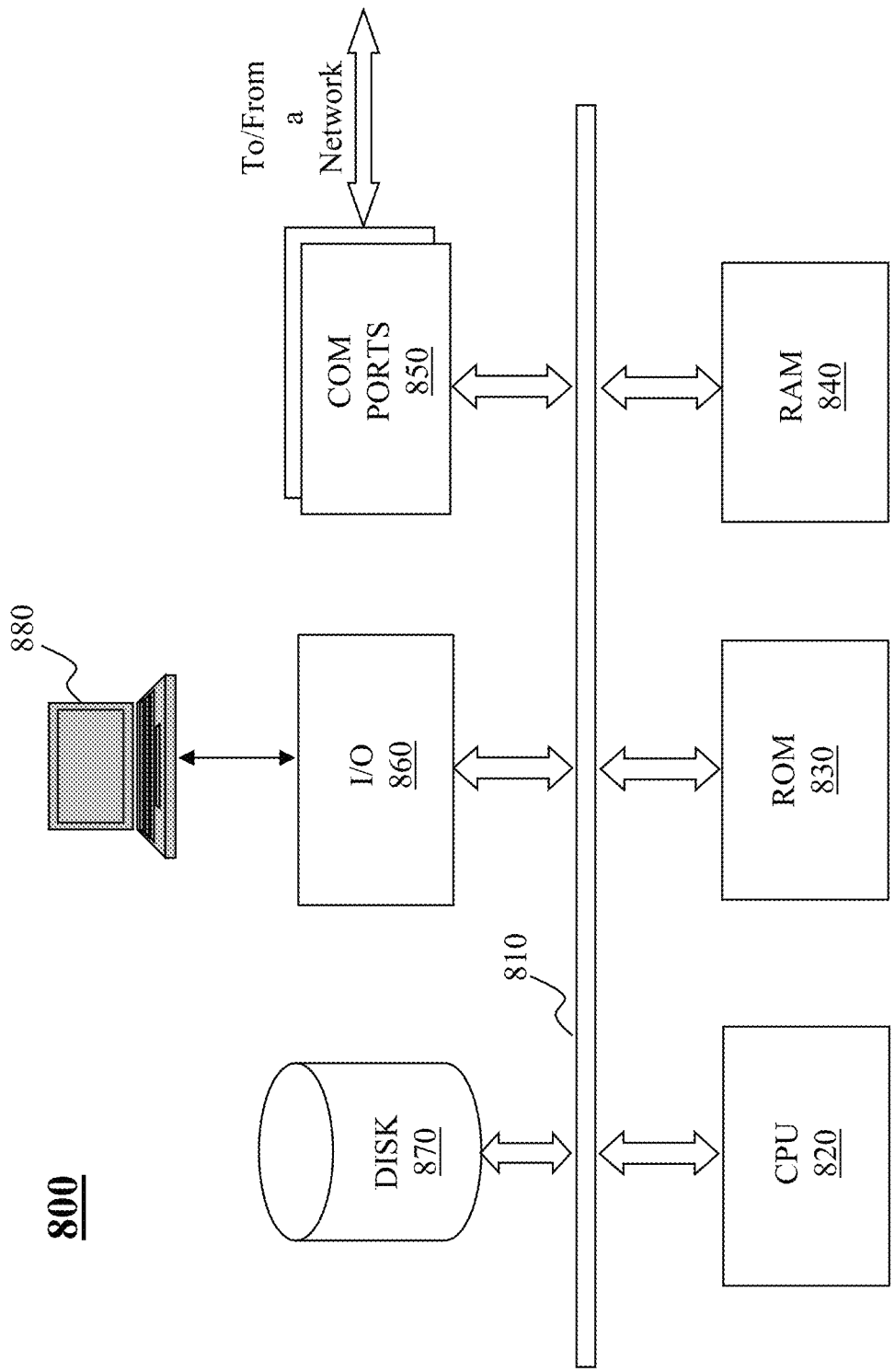
FIG. 8 is an illustrative diagram of an exemplary computing device architecture that may be used to realize a specialized system implementing the present teaching in accordance with various embodiments.

FIG. 8 is an illustrative diagram of an exemplary computing device architecture that may be used to realize a specialized system implementing the present teaching in accordance with various embodiments. Such a specialized system incorporating the present teaching has a functional block diagram illustration of a hardware platform, which includes user interface elements. The computer may be a general-purpose computer or a special purpose computer. Both can be used to implement a specialized system for the present teaching. This computer 800 may be used to implement any component or aspect of the framework as disclosed herein. For example, the information analytical and management method and system as disclosed herein may be implemented on a computer such as computer 800, via its hardware, software program, firmware, or a combination thereof. Although only one such computer is shown, for convenience, the computer functions relating to the present teaching as described herein may be implemented in a distributed fashion on a number of similar platforms, to distribute the processing load.

Computer 800, for example, includes COM ports 850 connected to and from a network connected thereto to facilitate data communications. Computer 800 also includes a central processing unit (CPU) 820, in the form of one or more processors, for executing program instructions. The exemplary computer platform includes an internal communication bus 810, program storage and data storage of different forms (e.g., disk 870, read only memory (ROM) 830, or random-access memory (RAM) 840), for various data files to be processed and/or communicated by computer 800, as well as possibly program instructions to be executed by CPU 820. Computer 800 also includes an I/O component 860, supporting input/output flows between the computer and other components therein such as user interface elements 880. Computer 800 may also receive programming and data via network communications.

Hence, aspects of the methods of information analytics and management and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, in connection with information analytics and management. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution, e.g., an installation on an existing server. In addition, the techniques as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method implemented on at least one processor, a memory, and a communication platform, comprising:
   receiving an input associated with a three-dimensional (3D) object with multiple regions therein;
   obtaining a 3D volumetric model characterizing the 3D object, wherein the 3D object includes multiple regions, each of which occupies a plurality of voxels in the 3D volumetric model, voxels of each of the multiple regions have the same label, and voxels in different regions of the 3D object are assigned with different labels;
   generating a 3D surface mesh representation characterizing the surface of the 3D object, wherein the 3D surface mesh representation comprises a plurality of connected geometric units, wherein each of the geometric units is defined by a plurality of vertices;
   identifying region boundaries on the surface of the 3D object based on the 3D surface mesh representation and the 3D volumetric model, wherein identifying the region boundaries comprises:
      determining, with respect to each vertex of each of the geometric units, a vertex label based on a voxel label assigned to a voxel from the 3D volumetric model, wherein the vertex interfaces with the voxel; and
      assigning the voxel label to the vertex;
   rendering the 3D object on a two-dimensional (2D) display device; and
   overlaying the region boundaries of the 3D object on the rendered 3D object.

2. The method of claim 1, wherein
the 3D object corresponds to a human liver or a resection region of the human liver; and
the multiple of regions correspond to lobes of the 3D object; and
the resection region is defined based on an abnormal growth detected inside the human liver.

3. The method of claim 1, wherein
each of the geometric units has a geometric shape, corresponding to one of a triangle, a rectangle, and a square.

4. The method of claim 1, further comprising:
designating each of the geometric units of the 3D surface mesh representation that has vertices with different vertex labels as a region boundary unit; and
generating the region boundaries on the surface of the 3D object based on the region boundary units.

5. The method of claim 1, wherein overlaying the region boundaries comprises:
determining a perspective by which the 3D object is rendered on the 2D display device;
registering the region boundaries on the surface of the 3D object based on the perspective; and
projecting each of the geometric units in the region boundaries onto the 2D display device based on the registration result.

6. Machine readable medium having information recorded thereon, wherein the medium, when read by the machine, causes the machine to perform the following steps:
   receiving an input associated with a three-dimensional (3D) object with multiple regions therein;
   obtaining a 3D volumetric model characterizing the 3D object, wherein the 3D object includes multiple regions, each of which occupies a plurality of voxels in the 3D volumetric model, voxels of each of the multiple regions have the same label, and voxels in different regions of the 3D object are assigned with different labels;
   generating a 3D surface mesh representation characterizing the surface of the 3D object, wherein the 3D surface mesh representation comprises a plurality of connected geometric units, wherein each of the geometric units is defined by a plurality of vertices;
   identifying region boundaries on the surface of the 3D object based on the 3D surface mesh representation and the 3D volumetric model, wherein identifying the region boundaries comprises:
      determining, with respect to each vertex of each of the geometric units, a vertex label based on a voxel label assigned to a voxel from the 3D volumetric model, wherein the vertex interfaces with the voxel; and assigning the voxel label to the vertex;
rendering the 3D object on a two-dimensional (2D) display device; and
overlaying the region boundaries of the 3D object on the rendered 3D object.

7. The medium of claim 6, wherein
the 3D object corresponds to a human liver or a resection region of the human liver; and
the multiple of regions correspond to lobes of the 3D object; and
the resection region is defined based on an abnormal growth detected inside the human liver.

8. The medium of claim 6, wherein
each of the geometric units has a geometric shape, corresponding to one of a triangle, a rectangle, and a square.

9. The medium of claim 6, wherein the information, when read by the machine, further causes the machine to perform:
designating each of the geometric units of the 3D surface mesh representation that has vertices with different vertex labels as a region boundary unit; and
generating the region boundaries on the surface of the 3D object based on the region boundary units.

10. The medium of claim 6, wherein overlaying the region boundaries comprises:
determining a perspective by which the 3D object is rendered on the 2D display device;
registering the region boundaries on the surface of the 3D object based on the perspective; and
projecting each of the geometric units in the region boundaries onto the 2D display device based on the registration result.

11. A system, comprising:
a 3D region volume modeling unit implemented by a processor and configured for:
  receiving an input associated with a three-dimensional (3D) object with multiple regions therein, and
  obtaining a 3D volumetric model characterizing the 3D object, wherein the 3D object includes multiple regions, each of which occupies a plurality of voxels in the 3D volumetric model, voxels of each of the multiple regions have the same label, and voxels in different regions of the 3D object are assigned with different labels;
a mesh-based region boundary determiner implemented by a processor and configured for
generating a 3D surface mesh representation characterizing the surface of the 3D object, wherein the 3D surface mesh representation comprises a plurality of connected geometric units, wherein each of the geometric units is defined by a plurality of vertices; and
identifying region boundaries on the surface of the 3D object based on the 3D surface mesh representation and the 3D volumetric model, wherein identifying the region boundaries comprises:
  determining, with respect to each vertex of each of the geometric units, a vertex label based on a voxel label assigned to a voxel from the 3D volumetric model, wherein the vertex interfaces with the voxel; and
  assigning the voxel label to the vertex; and
a region boundary overlay display unit implemented by a processor and configured for rendering the 3D object on a two-dimensional (2D) display device, and
overlaying the region boundaries of the 3D object on the rendered 3D object.

12. The system of claim 11, wherein
the 3D object corresponds to a human liver or a resection region of the human liver; and
the multiple of regions correspond to lobes of the 3D object; and
the resection region is defined based on an abnormal growth detected inside the human liver.

13. The system of claim 11, wherein
each of the geometric units has a geometric shape, corresponding to one of a triangle, a rectangle, and a square.

14. The system of claim 11, wherein the mesh-based region boundary determiner further comprises:
a mesh unit based boundary identifier implemented by a processor and configured for
  designating each of the geometric units of the 3D surface mesh representation that has vertices with different vertex labels as a region boundary unit, and
  generating the region boundaries on the surface of the 3D object based on the region boundary units.

15. The system of claim 11, wherein the region boundary overlay display unit performs overlaying the region boundaries by:
determining a perspective by which the 3D object is rendered on the 2D display device;
registering the region boundaries on the surface of the 3D object based on the perspective; and
projecting each of the geometric units in the region boundaries onto the 2D display device based on the registration result.

* * * * *